US011406867B1

(12) United States Patent
Beck et al.

(10) Patent No.: US 11,406,867 B1
(45) Date of Patent: Aug. 9, 2022

(54) PORTABLE SYSTEM AND APPARATUS FOR DYNAMOMETRY, EXERCISE, AND REHABILITATION

(71) Applicant: United States of America as represented by the Administrator of NASA, Washington, DC (US)

(72) Inventors: Christopher E. Beck, Houston, TX (US); Eduardo Herrera, Houston, TX (US); Austin Lovan, Houston, TX (US); Jairo Sanchez, Houston, TX (US); Andrew S. Donnan, Houston, TX (US); Roger Rovekamp, Beavercreek, OH (US); Briana Luthman, Houston, TX (US); Edward B. Behan, Shirley, NY (US); Richard M. Prince, Shirley, NY (US); Arthur J. Lekstutis, Shirley, NY (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 284 days.

(21) Appl. No.: 16/663,053

(22) Filed: Oct. 24, 2019

Related U.S. Application Data

(60) Provisional application No. 62/750,239, filed on Oct. 24, 2018.

(51) Int. Cl.
*A63B 23/04* (2006.01)
*A63B 21/005* (2006.01)
(Continued)

(52) U.S. Cl.
CPC ......... *A63B 23/0494* (2013.01); *A61H 1/024* (2013.01); *A61H 1/0237* (2013.01);
(Continued)

(58) Field of Classification Search
CPC ............ A63B 21/0058; A63B 21/4047; A63B 23/0494; A63B 2208/0233;
(Continued)

(56) References Cited

U.S. PATENT DOCUMENTS

| 4,628,910 A | * | 12/1986 | Krukowski | ........ A63B 21/0058 |
| | | | | 601/26 |
| 4,691,694 A | | 9/1987 | Boyd et al. | |

(Continued)

OTHER PUBLICATIONS

Kollock et al., The Reliability of Portable Fixed Dynamometry During Hip and Knee Strength Assessments, Journal of Athletic Training, 2010, pp. 349-356.
(Continued)

*Primary Examiner* — Joshua Lee
(74) *Attorney, Agent, or Firm* — Kurt G. Hammerle; Edward K. Fein

(57) ABSTRACT

A portable system for dynamometry, exercise, and rehabilitation comprises a base, a detachable servomotor assembly, an embedded control system, and a physical human-machine interface for securing a human limb into a stabilized position for use in a repeatable and ambidextrous manner. In another embodiment, the portable system includes a power source and a user interface subsystem for selecting operative modes and input parameters and for real-time processing, display, and storage of the values collected by the system during operation. In another embodiment, a method for determining strength of an isolated muscle group of a human joint is disclosed. The method includes the steps of mounting and securing a detachable servomotor assembly of a portable dynamometer upon a surface and securing the human joint to be tested into a stable position with an adjustable, ambidextrous distal limb attachment assembly for use of the portable dynamometer in a readily repeatable manner.

19 Claims, 13 Drawing Sheets

(51) Int. Cl.
   *A63B 21/00*   (2006.01)
   *A61H 1/02*    (2006.01)
   *A61B 5/22*    (2006.01)

(52) U.S. Cl.
   CPC ...... *A63B 21/0058* (2013.01); *A63B 21/4047* (2015.10); *A61B 5/22* (2013.01); *A61B 5/224* (2013.01); *A61H 1/02* (2013.01); *A61H 2201/0149* (2013.01); *A61H 2201/0192* (2013.01); *A61H 2201/1215* (2013.01); *A61H 2201/163* (2013.01); *A61H 2201/1642* (2013.01); *A61H 2201/1671* (2013.01); *A61H 2201/5061* (2013.01); *A63B 2208/0233* (2013.01); *A63B 2210/02* (2013.01); *A63B 2220/16* (2013.01); *A63B 2220/54* (2013.01); *A63B 2225/09* (2013.01)

(58) Field of Classification Search
   CPC ............ A63B 2210/02; A63B 2220/16; A63B 2220/54; A63B 2225/09; A61B 5/22; A61B 5/224; A61H 1/02; A61H 1/0237; A61H 1/024; A61H 2201/0149; A61H 2201/0192; A61H 2201/1215; A61H 2201/163; A61H 2201/1642; A61H 2201/1671; A61H 2201/5061
   See application file for complete search history.

(56) References Cited

U.S. PATENT DOCUMENTS

| | | | | |
|---|---|---|---|---|
| 4,776,587 | A | * | 10/1988 | Carlson .............. A63B 23/0494 482/134 |
| 4,905,676 | A | * | 3/1990 | Bond .................... A63B 24/00 601/34 |
| 4,934,694 | A | * | 6/1990 | McIntosh .......... G05B 19/4142 482/9 |
| 5,209,223 | A | | 5/1993 | McGorry et al. |
| 5,244,441 | A | * | 9/1993 | Dempster ............. A63B 23/00 482/9 |
| 5,403,251 | A | * | 4/1995 | Belsito ................... G16H 20/30 482/4 |
| 2009/0012579 | A1 | * | 1/2009 | Perumal ............ A61N 1/36003 607/48 |
| 2012/0165158 | A1 | * | 6/2012 | Ren ................. A63B 21/00178 482/7 |
| 2014/0135174 | A1 | * | 5/2014 | Potash ............... A63B 23/0494 482/8 |
| 2016/0107021 | A1 | * | 4/2016 | Bakrac ............. A63B 23/0494 482/139 |

OTHER PUBLICATIONS

Comprehensive System for Objective Functional Capacity, BTE The Technology of Human Performance, www.btetech.com.

* cited by examiner

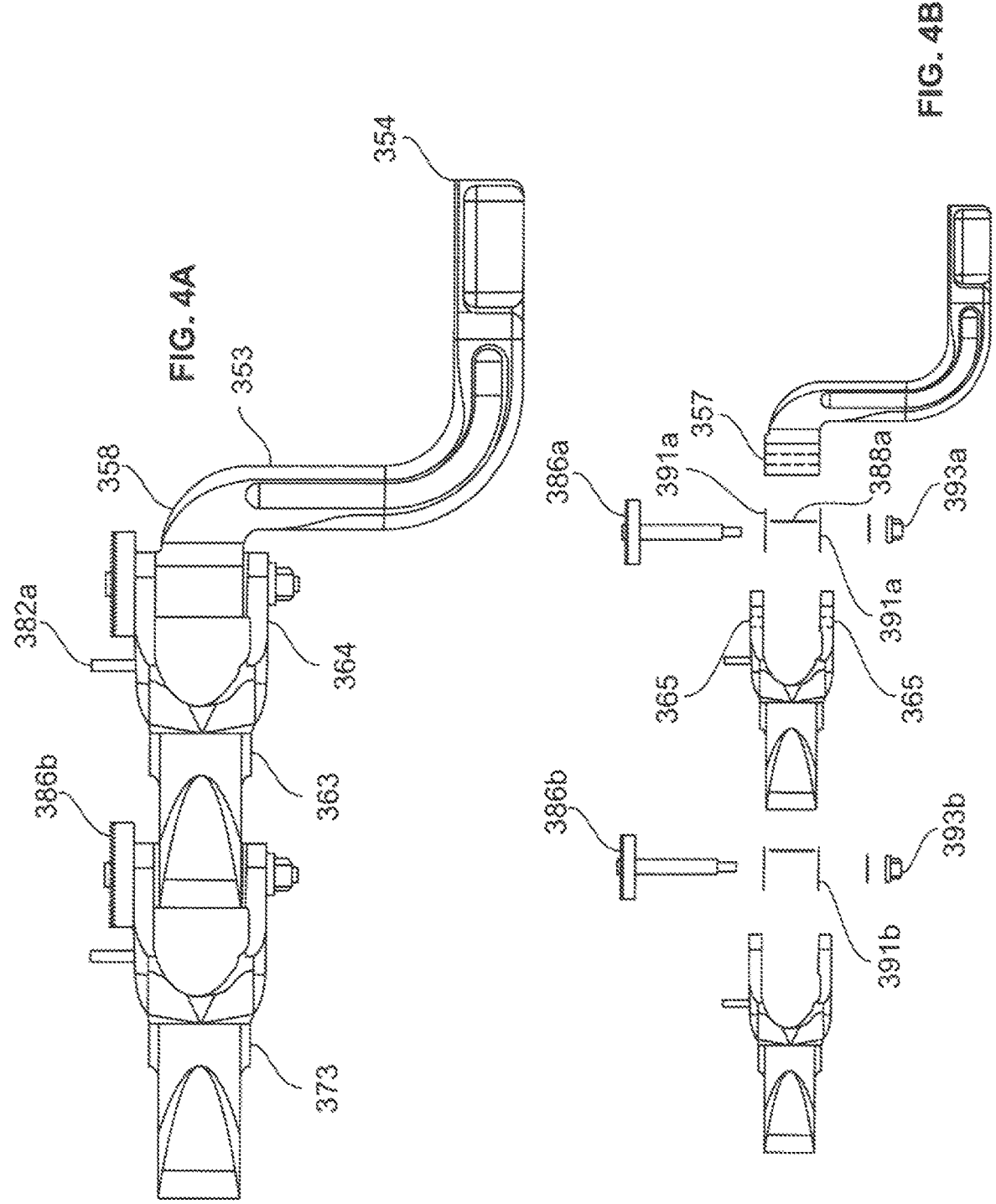

PORTABLE SYSTEM AND APPARATUS FOR DYNAMOMETRY, EXERCISE, AND REHABILITATION

CROSS-REFERENCE TO RELATED APPLICATIONS

This application claims priority to U.S. Provisional Patent Application No. 62/750,239, filed on Oct. 24, 2018, the entirety of which is incorporated by reference herein

ORIGIN OF INVENTION

The invention described herein was made in the performance of work under a NASA contract and is subject to the provisions of Section 305 of the National Aeronautics and Space Act of 1958, now codified at 51 U.S.C. 20135. The invention described herein was also made by employee(s) of the United States Government and may be manufactured and used by or for the Government of the United States of America for governmental purposes without the payment of any royalties thereon or therefor.

BACKGROUND

1. Field of Invention

The invention relates generally to the field of muscle exercise and rehabilitation and to the field of dynamometry.

2. Discussion of the Related Art

Dynamometry is a method to determine strength of isolated muscle groups. The process includes obtaining quantifiable measurements of muscular strength, power, and/or endurance. Existing systems are large, heavy, and constrained to one location, usually in a rehabilitation or physical therapy clinic. Thus, the market has a long-felt but unsolved need for a portable dynamometry system, allowing strength assessment, exercise, and rehabilitation to occur outside of a clinic, e.g., at a patient's home.

SUMMARY

In accordance with one embodiment described herein, a portable dynamometer measures strength of a muscle group of a human joint. The portable dynamometer comprises a base positioned and secured upon a surface and a servomotor or actuator assembly, operatively connected to the base and readily detachable therefrom, for measuring positional values and torque values associated with motion of the human joint. An embedded control system, operatively connected to the servomotor assembly and the base, controls rotational motion of a rotor located in the servomotor assembly and collects positional values and torque values measured by the servomotor assembly. A physical human-machine interface secures the human joint into a stable position for use of the portable dynamometer in an ambidextrous and readily repeatable manner. A user interface sub-system is provided for selecting operative modes and input parameters of the portable dynamometer and for real-time processing and display of collected values and storing of such collected values as electronic data. An electric power source such as an electric power cord supplies electrical power to the system.

In another embodiment, the physical human-machine interface is capable of readily making repeatable sizing adjustments to fit human test subjects within a large anthropometric range. The physical human-machine interface further comprises an adjustable set of straps, operatively connected to the base, one set of straps for stabilizing the human test subject at the thigh, the other set of straps stabilizing the human test subject at the waist and an adjustable ambidextrous distal limb attachment assembly, operatively connected to the servomotor assembly, the limb attachment assembly enabling multiple degrees of freedom for positioning and securing to a limb of the human test subject sized within a large anthropometric range.

In another embodiment, an exercise and rehabilitation apparatus comprises a base such as a seat plate positioned and secured upon a surface and a servomotor or actuator assembly, operatively connected to the base and readily detachable therefrom, for measuring positional values and torque values associated with motion of a human joint. An embedded control system, operatively connected to the servomotor assembly and the base, controls rotational motion of a rotor located in the servomotor assembly, and it collects positional values and torque values measured by the servomotor assembly. A physical human-machine interface secures the human joint into a stable position for use of the apparatus in an ambidextrous and readily repeatable manner. A user interface sub-system enables a user of the apparatus to select operative modes and input parameters of the apparatus and performs real-time processing and display of the collected positional and torque values, which may be stored as electronic data. An electric power source such as an electric power cord supplies electrical power to the apparatus.

In another embodiment, a method for determining strength of an isolated muscle group of a human joint, comprises the steps of: mounting and securing a detachable servomotor assembly of a portable dynamometer upon a surface; securing the human joint to be tested into a stable position with an adjustable, ambidextrous distal limb attachment assembly for use of the portable dynamometer in a readily repeatable manner; selecting an operative mode of the portable dynamometer; powering rotational motion of the detachable servomotor assembly when required for the selected operative mode; controlling rotational motion of the detachable servomotor assembly; measuring positional values and torque values associated with motion of the stabilized human joint; and collecting the positional values and the torque values that are measured by the detachable servomotor assembly.

Other aspects and advantages of the embodiments described herein will become apparent from the following description and appended claims, taken in conjunction with the accompanying drawings, illustrating the principles of the embodiments by way of example only.

BRIEF DESCRIPTION OF THE DRAWINGS

FIGS. 4A-4C are additional detailed views of the component parts of the adjustable, ambidextrous distal limb attachment assembly of FIGS. 2 and 3A-3C.

DETAILED DESCRIPTION OF EXEMPLARY EMBODIMENTS

Figure 1:
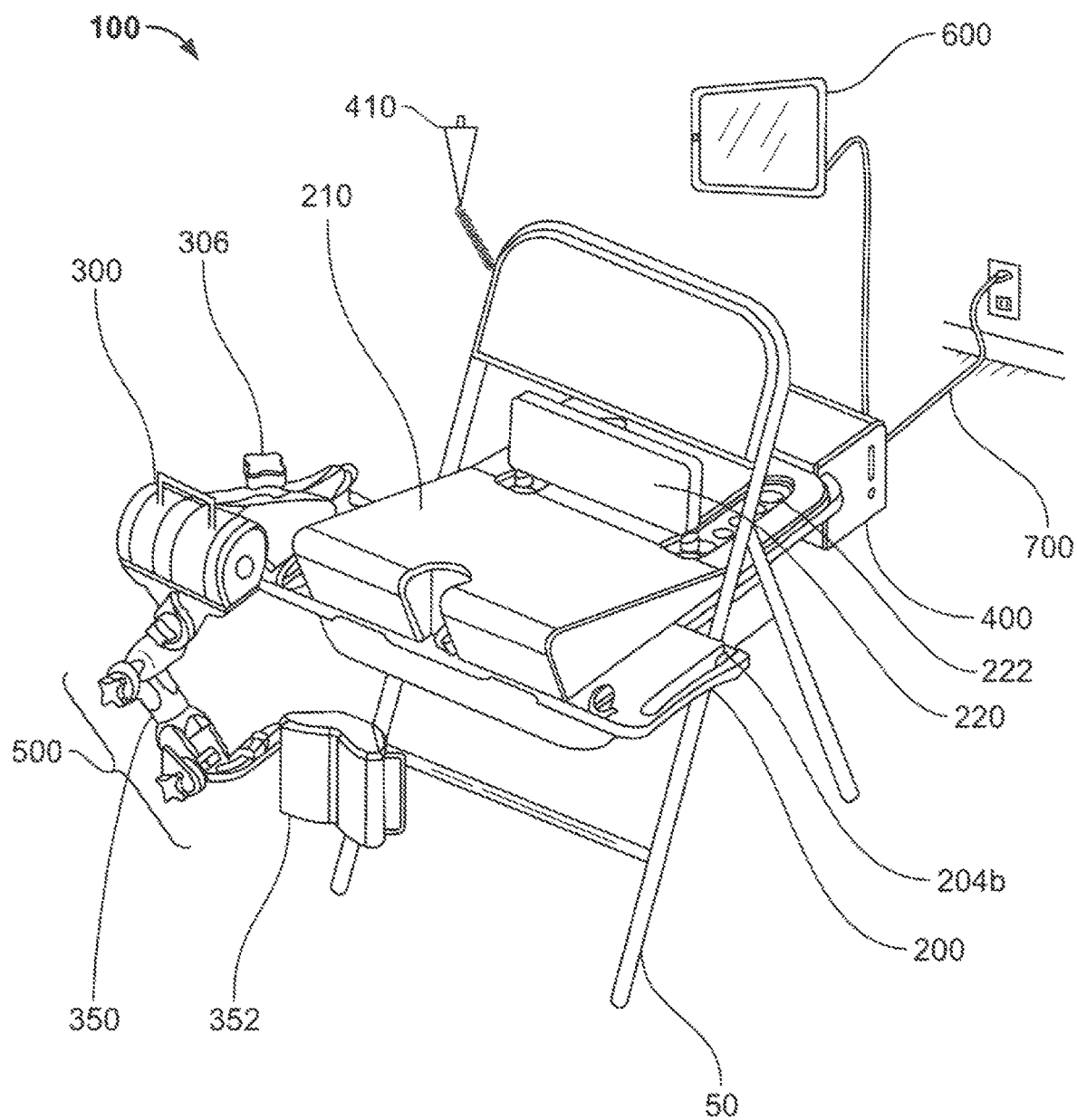
FIG. 1 is a perspective view of a portable dynamometer or apparatus as described herein positioned and secured mounted upon a surface, shown in this example to be a folding chair.
Figure 2:
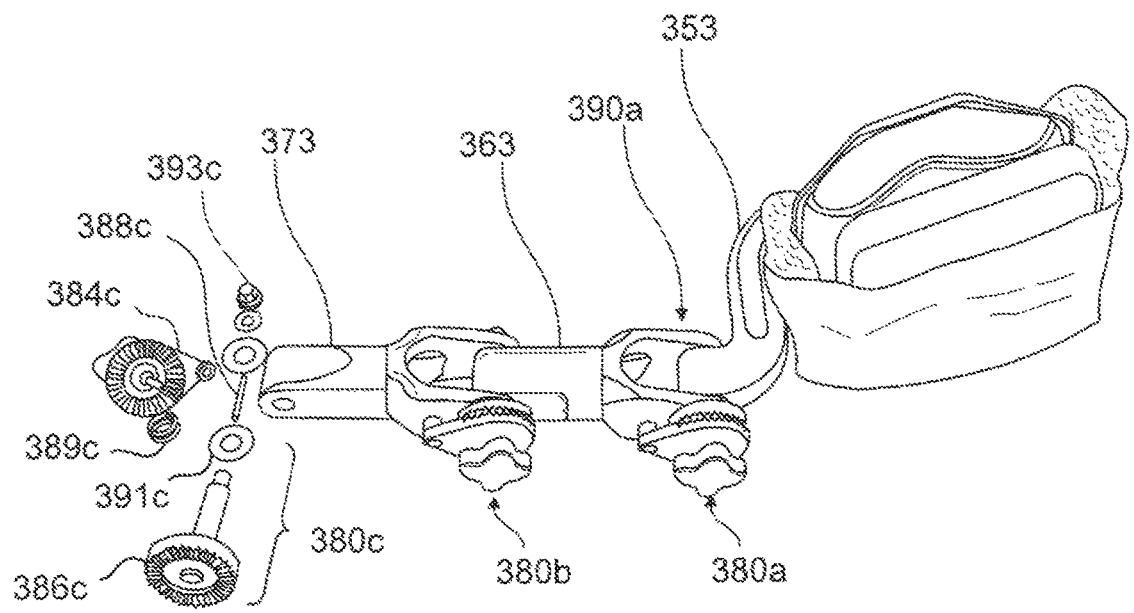
FIG. 2 is a perspective view of an adjustable, ambidextrous distal limb attachment assembly in accordance with one of the embodiments described herein.

Exemplary embodiments of the invention will now be described with reference to the accompanying figures. Like elements or components in the figures are denoted with the same reference characters for consistency.

Before beginning a detailed description of some exemplary embodiments of the invention, the meaning of certain terms as used herein will be given.

The term "ambidextrous" means designed or suitable for use on both sides of the human body, e.g., suitable for use on the left side or the right side of a human. The term also means versatile or reversible.

The term "isokinetic dynamometry" is a method of measuring strength of an isolated muscle group by measuring force of such muscle group when in movement while simultaneously measuring or controlling the velocity of such movement. Isokinetic dynamometers perform this method by controlling the velocity of the movement and measuring, at the same time, via a strain gauge force transducer or other sensor, the force exerted by the isolated muscle group.

The term "isokinetic exercise" is an exercise that provides a variable resistance to a constant limb movement.

The term "user-specified" means an operative mode in which an operator of the system or apparatus as described herein has selected an input or value.

As described herein, the embodiments include a portable dynamometer, a portable rehabilitation apparatus, a portable exercise apparatus, and an exercise and rehabilitation apparatus. In another embodiment, a method for determining strength of an isolated muscle group of a human joint is described using a portable dynamometer. The portable system/apparatus can be mounted on a variety of surface platforms including a portable folding chair or a table. A human test subject (patient) or a "user" of the exercise/rehabilitation apparatus is positioned and stabilized before operation of the system or apparatus. In one embodiment, the patient's (or user's) joint is placed in a location such that it has its axis of rotation substantially aligned collinearly with an axis of rotation of a servomotor/actuator assembly of the system. In another embodiment, the patient/user is securely strapped to the system/apparatus at the user's waist, thigh, and shank for dynamometry/exercise/rehabilitation of the knee. An adjustable backrest is operatively connected to a base or seat plate. An adjustable distal limb attachment assembly is operatively connected to the readily detachable servomotor assembly. The adjustable distal limb attachment assembly enables multiple degrees of freedom for positioning an adjustable limb assembly such that the user's knee (or other joint of interest for dynamometry, exercise, or rehabilitation) is stabilized as it rotates about an axis of rotation that is substantially collinear with an axis of rotation of the servomotor assembly. The base or seat plate is configured to be "ambidextrous" in the sense that the base enables a secured mounting of the servomotor assembly that is also readily detachable for reattaching to the base on the contralateral side of the patient's (or user's) body. e.g., both the right side and the left side of the patient/user. In one embodiment, the dynamometer is designed for stabilizing a human joint such as a knee. In another embodiment, the dynamometer is designed to fit and stabilize a human joint of humans within a large anthropometric range. In yet another embodiment, the large anthropometric range of humans starts from about the smaller $5^{th}$ percentile to about the larger $95^{th}$ percentile of adult humans (male and female). In yet another embodiment, the large anthropometric range of humans starts from about the smaller $10^{th}$ percentile to about the larger $90^{th}$ percentile of adult humans (male and female).

The embodiments described herein provide muscle strength assessment/rehabilitation/exercise capabilities by powering and controlling the servomotor assembly in a mode specified by the user or operator of the system/apparatus. Modes of operation include: (a) isokinetic concentric, where the apparatus or system limits a patient's/user's velocity to a setpoint; (b) passive, where the apparatus or system oscillates the patient's/users limb back and forth and the patient/user is instructed to attempt to resist the motion (although the apparatus/system overpowers the user and maintains its setpoint velocity); and (c) isometric, where the apparatus/system holds position against all pushes and pulls of a patient/user.

Referring now to FIG. 1, an exemplary embodiment of a portable system 100 provides a rehabilitation apparatus, an exercise apparatus, and an apparatus for dynamometry as shown in a perspective view of in accordance with one of the embodiments described herein. The system/apparatus 100 is shown positioned and secured upon a surface, in this embodiment a portable folding chair 50. The portable system 100 comprises in one embodiment a base or seat plate 200. As will be described with reference to the physical human-machine interface 500 of FIGS. 5A and 5B, the base 200 may have a seat cushion 210 positioned thereon and have an adjustable backrest 220 integrated therein. A set of straps 230/240 (not shown in FIG. 1 but visible in FIGS. 5A and 5B) or other similar strapping mechanism is used to position and secure the base 200 onto the surface, e.g., folding chair 50. The folding chair 50 as shown in FIG. 1 is one example of a surface used for mounting of the base 200, due to the ubiquity of such metal folding chairs at locations to which the system 100 might be transported.

A physical human-machine interface 500 is shown generally in FIG. 1. The physical human-machine interface 500 secures a human joint, such as a knee in the structural embodiments of FIGS. 1, 5A and 5B, into a stable position for use of the portable dynamometer 100 in an ambidextrous and readily repeatable manner. A removable and repositionable servomotor assembly 300 is operatively connected to the base 200 and is readily detachable therefrom. An adaptable distal limb attachment assembly 350, when combined with the servomotor assembly 300, enables quick, versatile, "ambidextrous" operation of the system/apparatus 100 on either side of the patient/user, without an additional motor or attachment mechanism for each side. In one embodiment, the physical human-machine interface 500 comprises the adaptable distal limb attachment assembly 350 in combination with a set of securing straps 230/240. In another embodiment, the physical human-machine interface 500 may further comprise the angled seat cushion 210 and the adjustable backrest 220 in addition to the assembly 350 and the set of straps 230/240. The distal limb attachment assembly 350 connects at rotatable output yoke 308 to enable motor-controlled motion of a lever link assembly (see FIGS. 2-4C). The limb attachment assembly 350 includes a distal limb cuff 352 and enables multiple degrees of freedom for positioning upon and stabilizing of a human joint.

Affixed to a rear or backend of the base 200 is an embedded control system 400, which provides functional control of the operative modes of the servomotor assembly, implements a safety protocol, computes rotational velocity of a rotor and enables collection of data reflective of position, rotational velocity, and force (torque) measurements taken by a sensor assembly 330 of the servomotor assembly 300, including isokinetic dynamometry. The system 100 further comprises a user interface subsystem 600 for selecting operative modes and input parameters of the portable system and for real-time display of system data collection. Such user interface sub-system 600 may comprise a computer (desktop or laptop), tablet, smart phone, smart watch, or other computing device having an electronic display and configured with an application or similar set of instructions to enable an operator and/or user of the system 100 to select a mode of operation of the embedded control system 400. In one embodiment, a wireless connection via a localized network operatively connects the control system 400 to the user interface 600. In another embodiment, such as the one shown in FIG. 1, a wired connection such as a Universal Serial Bus (USB) interface port or other comparable interface port is used. In one embodiment, a method of performing the user interface includes use of a graphical user interface or GUI for selection and use of the application. The system 100 further comprises an electric power source 700 such as a 110-volt alternating current (AC) power cord. The portable system 100 once assembled, positioned, and secured on a patient/user enables exercise, rehabilitation, and dynamometry on both limbs of the user.

Figure 5A:
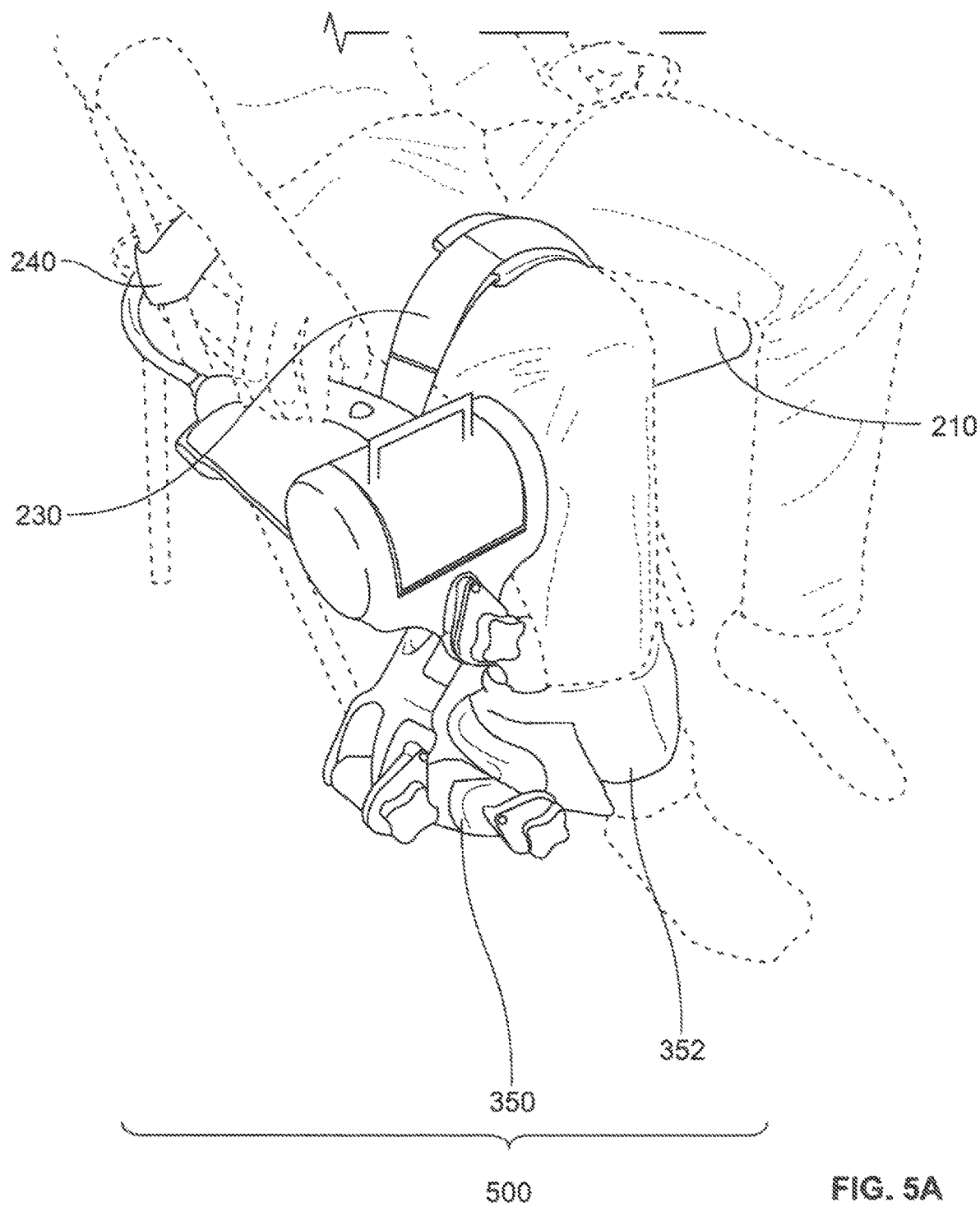
FIGS. 5A and 5B are perspective views of a human test subject positioned for strength testing by a dynamometer as described herein or of a user of an exercise and rehabilitation apparatus having a knee positioned and stabilized to a physical human-machine interface in accordance with one or more of the embodiments described herein.
Figure 5B:
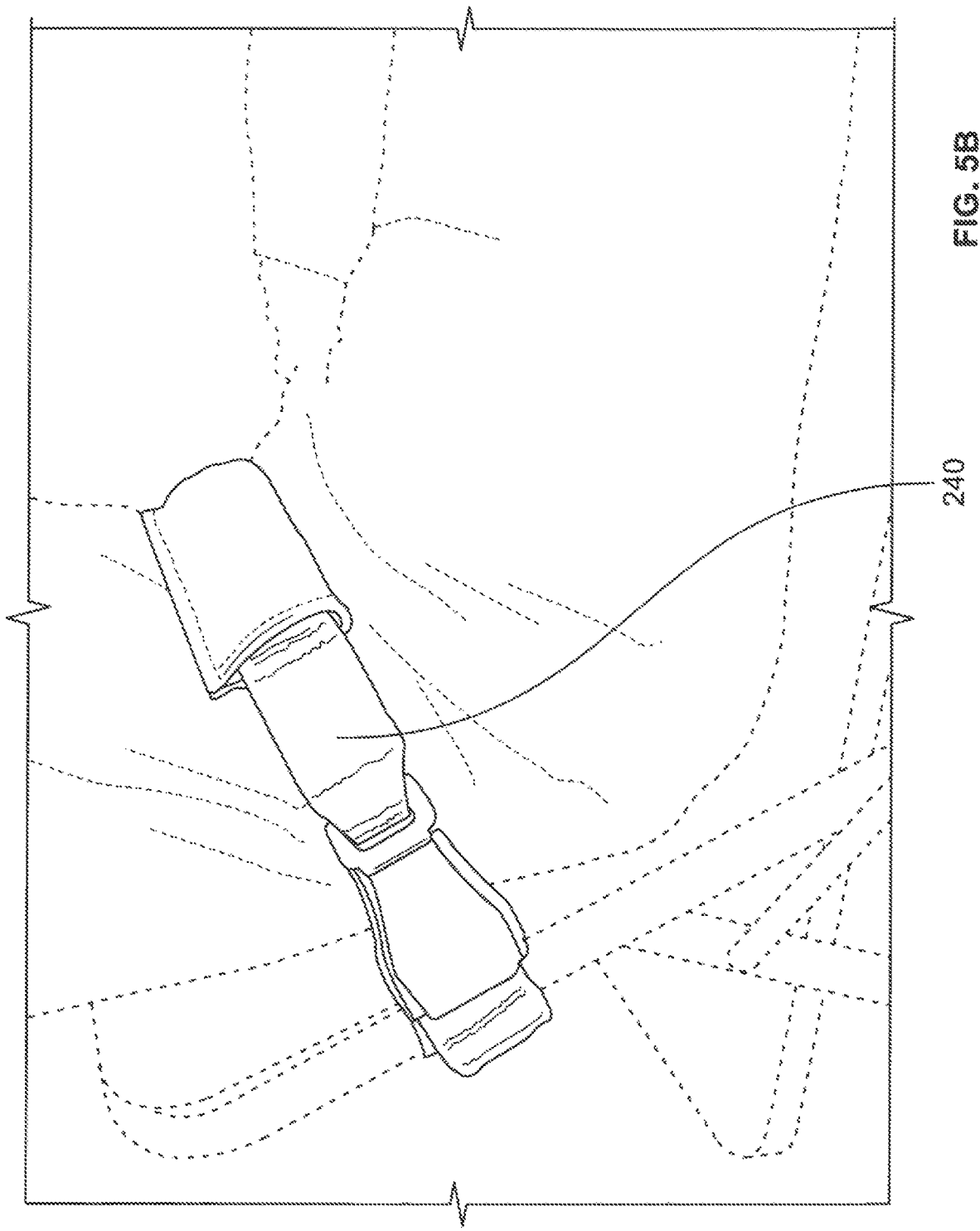

Referring now to FIGS. 5A and 5B, an embodiment of the system 100 is shown with a patient/user positioned onto the seat cushion 210. This embodiment shows in more detail the physical human-machine interface 500. As shown in this embodiment, the physical human-machine interface 500 includes a seat cushion 210, an adjustable seat backrest 220, a thigh strap 230, and a waist strap 240, with each set of straps being adjustable and operatively connected to the base 200 or a portable chair (as shown in FIG. 5B) for securing a patient/user at the thigh and waist. In this embodiment, the adjustable, "ambidextrous" distal limb attachment assembly 350, is also operatively connected to the removable servomotor assembly 300 at output yoke 308. The limb attachment assembly 350 with distal limb cuff 352 also enables multiple degrees of freedom for positioning and securing to the joint of the patient/user.

Referring to FIG. 1 and FIGS. 5A and 5B, the physical human-machine interface 500 is operatively connected to the base 200 and aids in securing the base to the surface of operation (chair 50). The interface 500 places the human joint, such as a knee in the structural embodiment of FIGS. 1, 5A and 5B, into a stable position for use of the system/apparatus. The physical human-machine interface 500 removes the need of two separate attachments for use of system on both left and right sides of the user. The base 200 has a series of pin receptacles 222 that allow for pins of backrest 220 to be adjusted into different positions depending on the size of the patient/user. The base 200 also includes a pair of servomotor receptacles 204a/204b for interchangeable swapping of the servomotor assembly on both the left and rights sides as will be described in further detail later herein. The seat cushion 210 is firm, and in one embodiment, including a slight pitch at an angle from a horizontal surface allowing an approximately horizontal femur position for most humans when sitting.

Referring again to FIG. 1, because the backrest 220 is adjustable on the base (seat plate) 200, it accommodates in one embodiment the $5^{th}$ to $95^{th}$ percentile of human femur lengths. The thigh strap 230 attaches to the base 200 between the legs, and operatively connects to a fixed loop on the left or right side of the base, depending on which limb is being tested, exercised, or rehabilitated. The waist strap 240 in one embodiment loops around the back of folding chair 50, securing the user to the back of folding chair 50 for stability. The user's shank or shinbone is secured with a set of straps integrated with the cuff 352. Setup allows for flexion and extension of the knee or other joint within a subset of the standard range of motion of a healthy human.

Three exercise modes or modes of operation are available: Isometric, Isokinetic, and Passive. The characteristics of these three operative modes are given below:

Isometric—the system holds position; user applies load into the system by bending/extending.

Isokinetic—motion of the system is constrained to be below a velocity setpoint; user bends/extends/moves the knee or other joint for dynamometry, exercise, or rehabilitation, and the system limits the velocity.

Passive—the system is instructed to move at a defined velocity, with or without user input; the user is instructed to resist the motion, but the servomotor assembly 300 maintains a constant velocity. ("Passive" refers to the user; even with a passive user, the system moves.)

Referring now to FIGS. 2, 3A-3C, and 4A-4C, the distal limb attachment assembly 350 connects to the servomotor assembly 300 at its output yoke 308. Attachment assembly 350 converts rotational torque of the servomotor assembly 300 to a force at the patient's/user's distal limb portion (e.g., shank) at the cuff 352, or vice versa, depending on the operative mode of the system/apparatus 100. In the embodiments shown, three lever lock knobs 381a-c are available to lock and unlock the limb attachment assembly 350, resulting in both medial-lateral and proximal-distal degrees of freedom of the cuff 352 with respect to the user's distal limb and an angular degree of freedom to align the cuff 352 with the axis of the user's limb. The medial-lateral and proximal-distal degrees of freedom enable the patient/user or a physical therapist to attach the limb attachment assembly 350 quickly and comfortably to the limb (e.g., shank) for a large anthropometric range (as previously described herein) of patients/users.

Figure 3A:
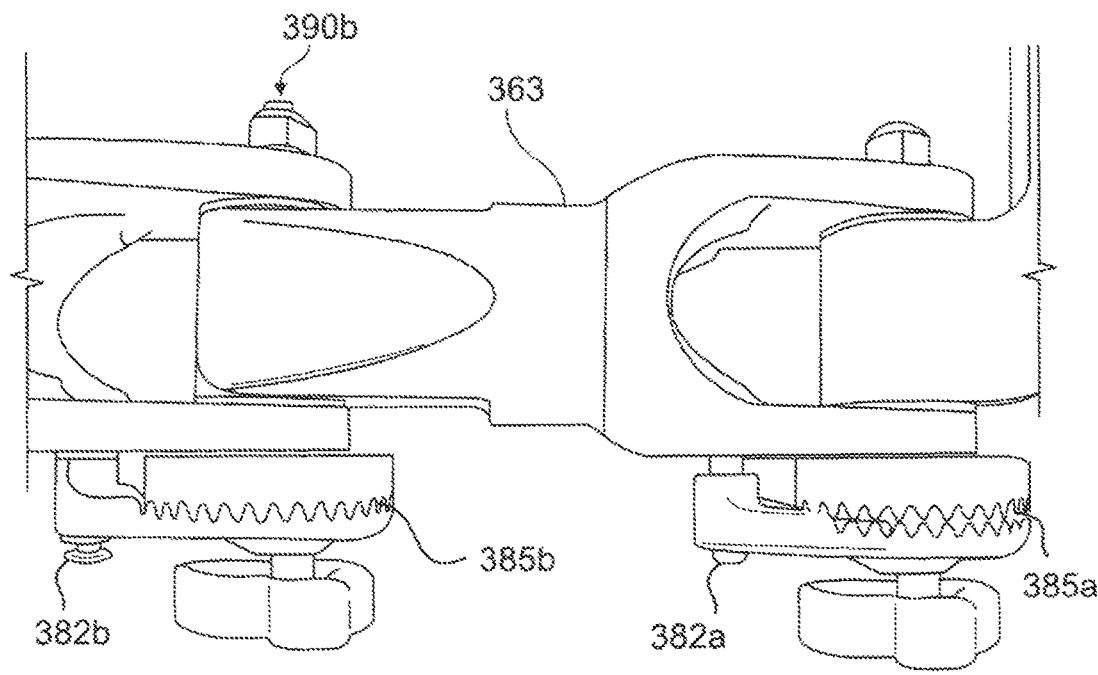
FIG. 3A provides a closer perspective view of a locking mechanism of the adjustable, ambidextrous distal limb attachment assembly of FIG. 2 in accordance with one of the embodiments described herein.
Figure 3B:
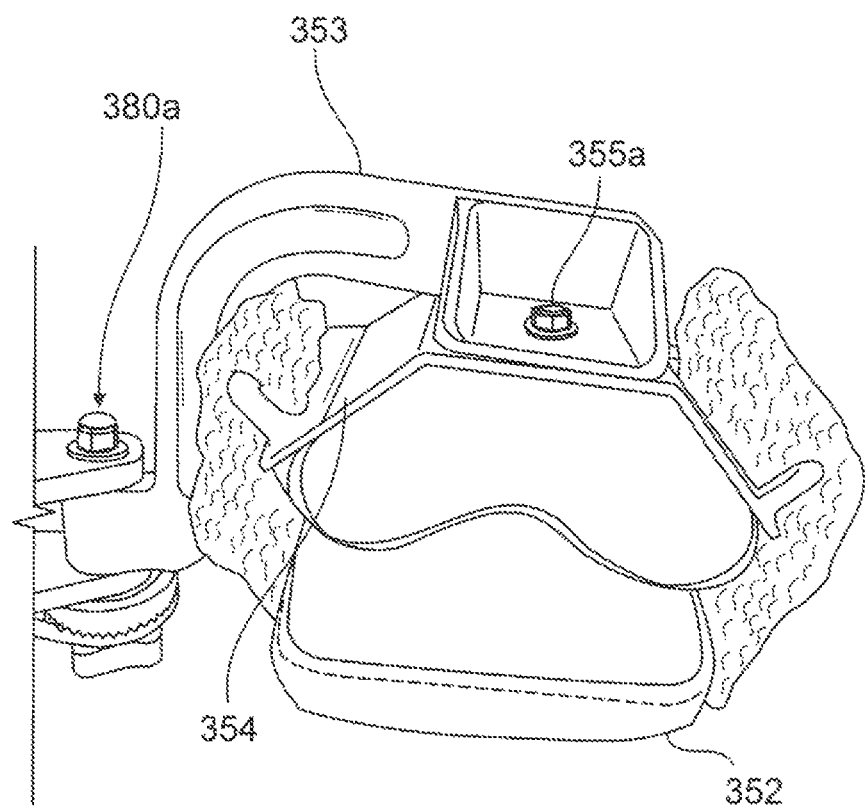
FIGS. 3B and 3C provide a side view and top view, respectively, of a cuff lever-link assembly in accordance with one of the embodiments described herein.
Figure 3C:
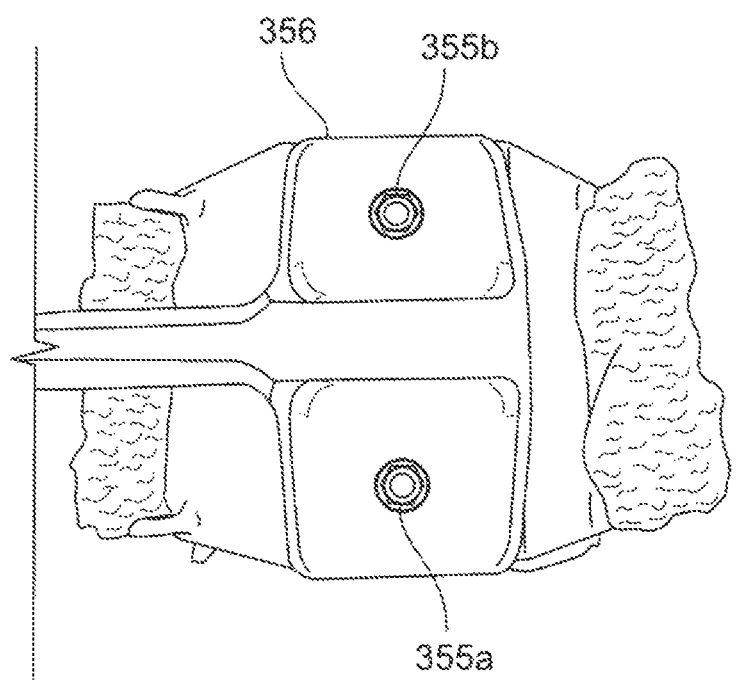
Figure 4C:
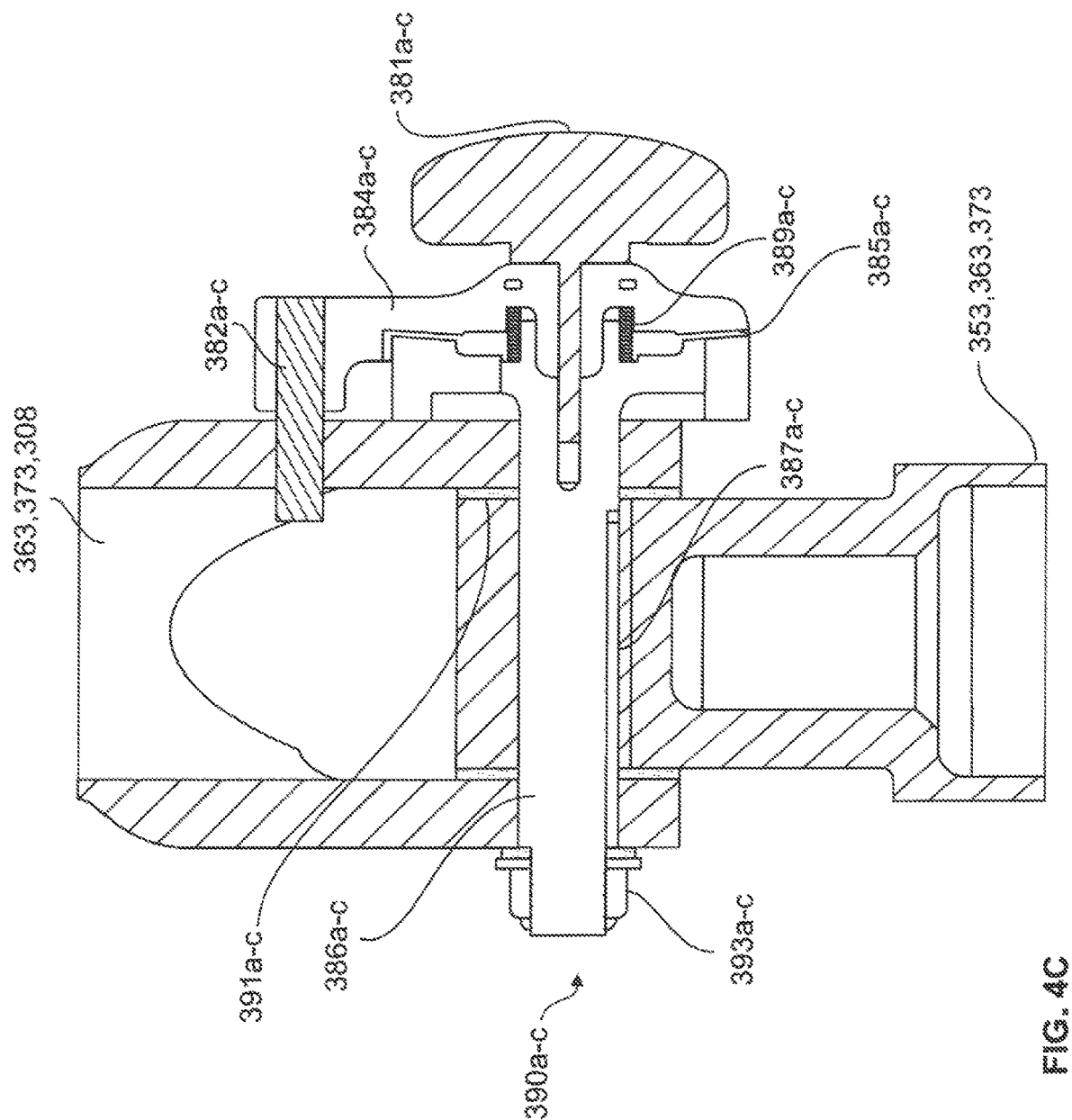

Continuing with reference to FIGS. 2, 3A-3C, and 4A-4C, the distal limb attachment assembly 350 comprises three linkages: curved lever link 353, a first straight lever link 363, and a second straight link 373. Each lever link 353, 363, 373 is adjustably joined to another lever link (or to output yoke 308) by a lever lock assembly 380 (shown in the locked position in FIG. 4C) to form a readjustable pivot joint 390. As shown in FIGS. 3B and 3C, the cuff 352 includes a supporting bracket 356 that is rigidly attached to the curved lever link 353 by a pair of flanged nuts 355a, 355b at a distal flanged end 354 of curved lever link 353.

To form a readjustable yet securable pivot joint 390 between the connected linkages, each lever lock assembly 380a-c comprises a lever lock knob (381a-c), an anti-rotation pin (382a-c), a lock plate (384a-c), a lock pin (386a-c), a lever lock key (388a-c), and a return spring (389a-c). For example, curved lever link 353 is connected to first straight lever link 363 by lever lock assembly 380a by aligning a pin hole 357 at proximal end 358 of the curved lever link 353 with the pair of distal pin holes 365 of clevis 364 of first lever link 363. A pair of thrust bearings 391a is positioned between the flat mating interior surfaces of the proximal end 358 and the clevis 364 of link 363. Lever lock key 388a is then positioned into a key slot of link 353. Next, lock pin 386a is positioned carefully to align with lock key 388a and is screwed into a position by threading into lock nut 393a until there is a light, even resistance through the full range of travel of the pivot joint being assembled. The lever lock key 388a ensures there is no rotation between the curved lever link 353 and the lock pin 386a along keyed interface 387a. Next, a hole in lock plate 384a slides over the anti-rotation pin 382a mounted into lever link 363. Lock plate 384a is then positioned such that its teeth can mate with the teeth of lock pin 386a to form a tapered teeth interface 385a therebetween. The lever lock knob 381a then passes through the lock plate 384a and threads into the lever lock pin 386a when it is turned clockwise by the user, which locks the rotation of the joint in place. These steps of assembly are repeated to interface the first straight lever link 363 with the second lever link 373 and to interface the second lever link 373 to the output yoke 308.

With a minimum of three adjustable pivot joints 390a-c using lever lock assemblies 380a-c as described above, the distal limb attachment assembly 350 allows medial-lateral and proximal-distal degrees of freedom while also allowing an angular degree of freedom for aligning the cuff 352 comfortably with the limb of the patient/user. Lever lock assemblies 380a-c can be repositioned when the teeth of the lock plate 384a-c are fully disengaged from the teeth of the lever lock pin 386a-c. The teeth disengage when the lever lock knob 381a-c is turned counter-clockwise. A return spring 389a-c keeps the corresponding lock plate 384a-c in contact with the corresponding lever lock knob 381a-c, ensuring the lever lock plate 384a-c separates from corresponding lock pin 386a-c as the lever lock knob 381a-c is loosened and unthreaded.

Figure 6A:
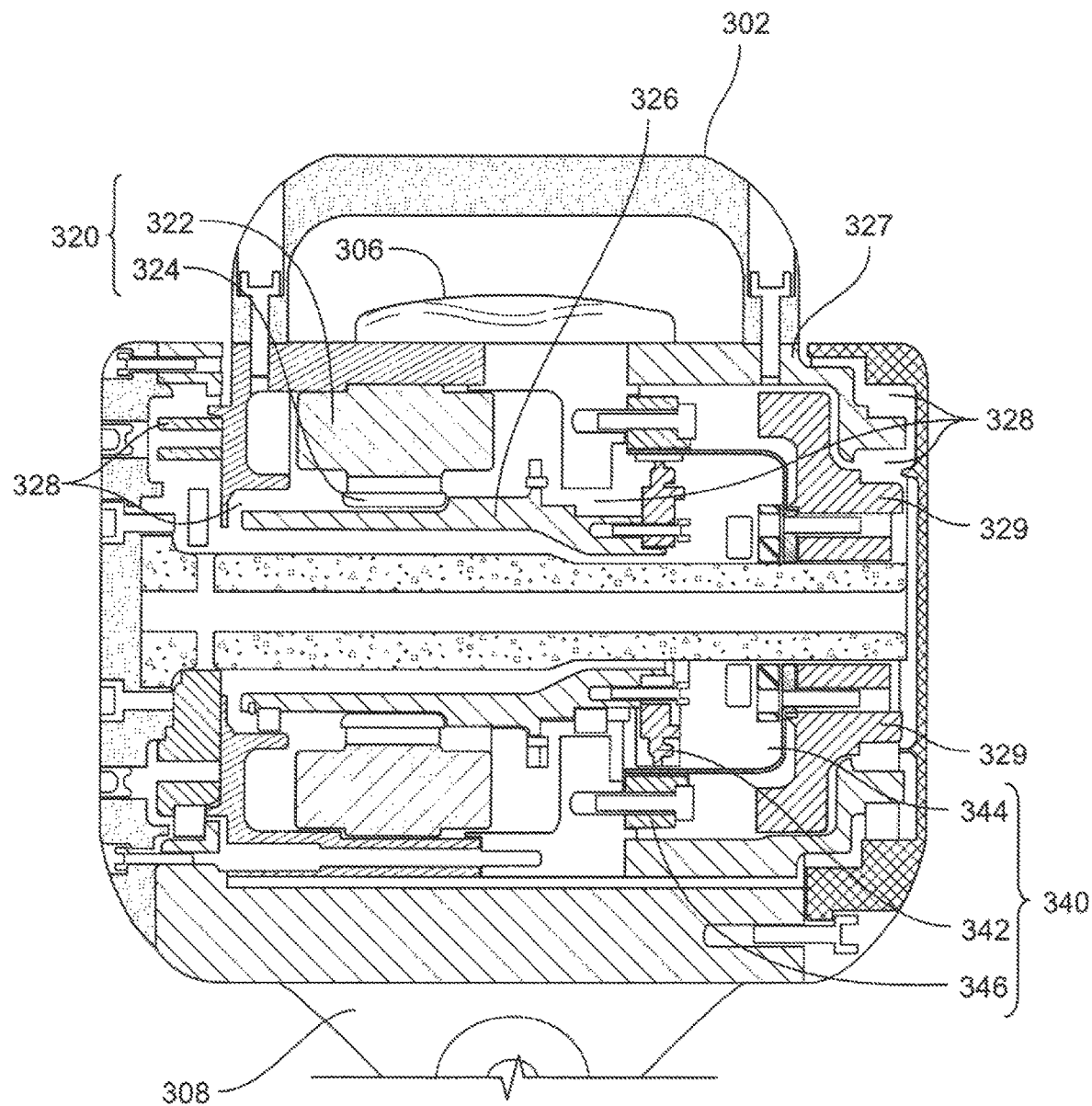
FIGS. 6A and 6B illustrate a front cross-sectional view and a top cross-sectional view, respectively, of a portion of a servomotor assembly detailing the operative components of this assembly having positional and force sensors for measuring positional and torque values.
Figure 6B:
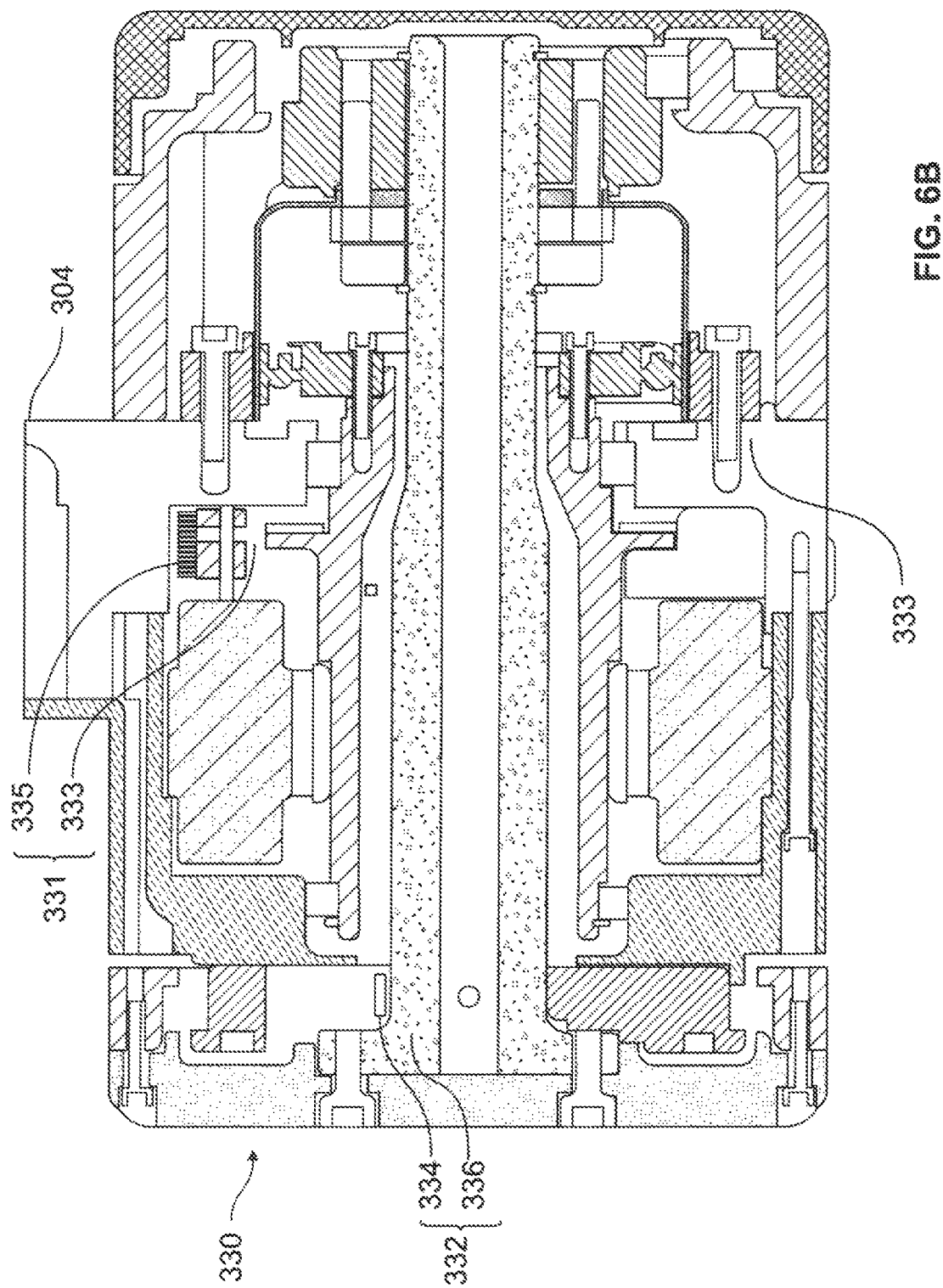
Figure 6C:
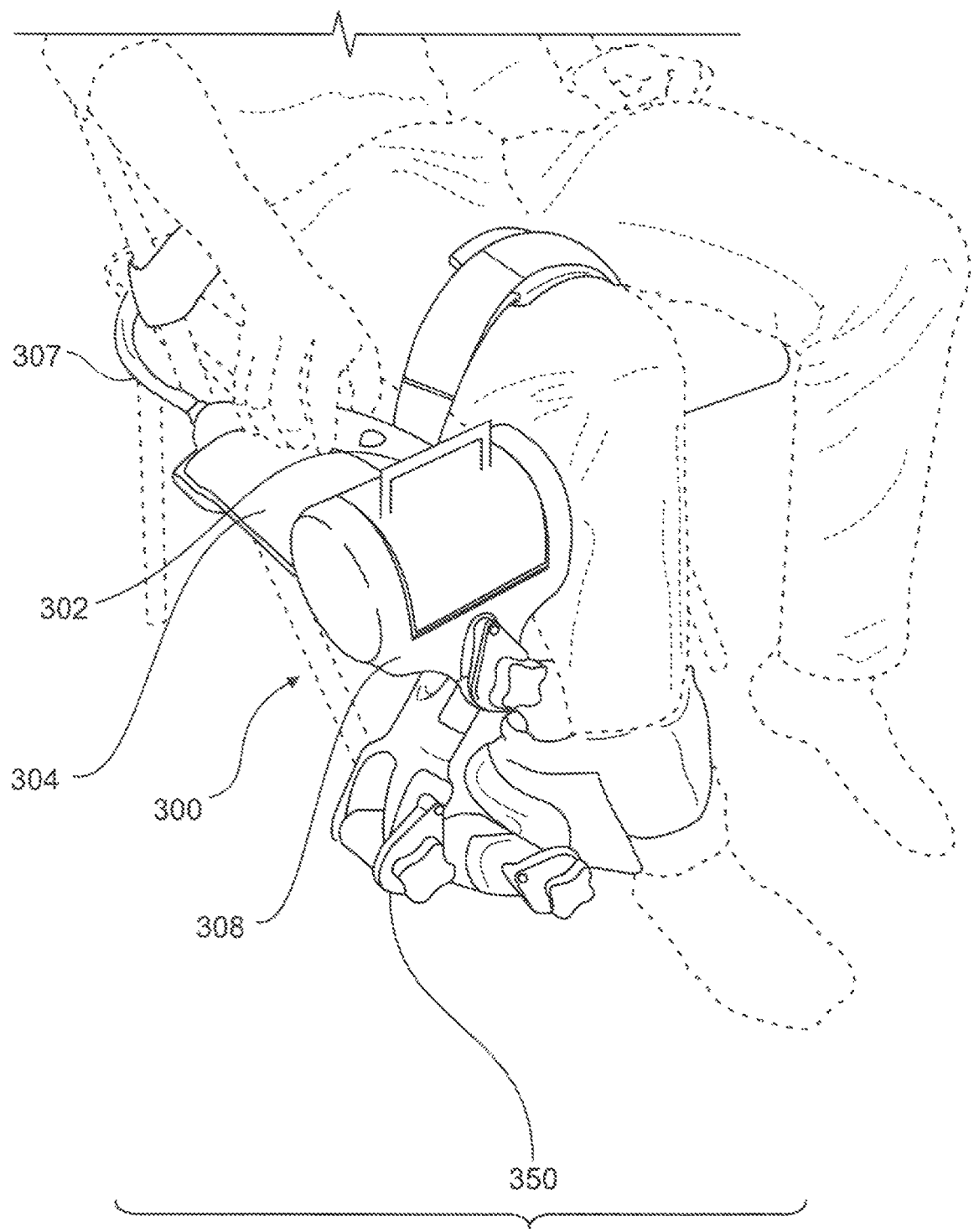
FIG. 6C is another perspective view of the servomotor assembly showing structural components for removing this assembly from one side of a patient or user and repositioning and securing to the contralateral side thereof.

Referring now to FIGS. 1 and 6C, the removable and repositionable servomotor assembly 300 can be quickly moved beside the right leg or the left leg of a patient/user. Repositioning can be readily achieved by unscrewing a knob/bone mounting assembly 306 and lifting the servomotor assembly 300 using handle 302 out of a first servomotor receptacle 204a (not shown in FIG. 1 because it is covered by assembly 300). The servomotor assembly 300 is then placed into a second servomotor receptacle 204b on the other side of the seat cushion 210 and secured by turning the knob of the knob/bone mounting assembly 306 until tight. Each servomotor receptacle 204a/204b comprises a pin and tapered interface, which minimizes imperfect alignment and creates a secure structural joint or connection between a structural bone 304 of the servomotor assembly 300 and the base 200.

The portable system 100 comprises structural hardware, a physical human-machine interface 500, electronics, electrical power supply (in one embodiment a 110V AC wall plug), and embedded firmware to operate the exercise and rehabilitation capabilities. The system in one embodiment receives input from an external computer or user interface subsystem 600 to enable operation. Communication architecture provides two-way transfer of command data and display/status data to interface subsystem 600. In one embodiment, all of the embedded control features of embedded control system 400 are closed-loop, meaning that the controls reside in the embedded control system 400, and the system 100 does not require communication with an external computer for any of the modes of operation described herein. In another embodiment, embedded control system 400 includes a comfort stop 410 to enable the user to inactivate quickly the motor of the servomotor/actuator assembly 300. In another embodiment, an embedded firmware subsystem of embedded control system 400 includes an additional safety monitoring functionality to disable power to servomotor assembly 300 in the event of limit exceedance.

Referring now to FIGS. 6A and 6B, the drawings illustrate a front cross-sectional view and a top cross-sectional view, respectively, of the servomotor assembly 30) to identify major operative components located within a housing of the assembly in accordance with embodiments described herein. With reference to FIG. 6A, the servomotor assembly 300 comprises a brushless DC motor 320 of the in-runner variety having a motor stator 322 and motor rotor 324. Motor rotor 324 is fixedly connected to a rotor shaft 326, which transfers rotational motion to a strain-wave gear transmission assembly 340 via a wave generator 342. The strain-wave gear transmission assembly 340 further comprises a flex spline 344 and a circular spline 346, which work together in combination to transfer rotational motion to output yoke 308. The strain-wave gear transmission assembly 340 provides a spatially compact method of high torque gear reduction without backlash. In one embodiment, the strain-wave gear transmission assembly implements an 80:1 gear reduction. Examples of strain-wave gear transmission assemblies available commercially include ones sold by Harmonic Drive of Peabody, Mass. and Cone Drive of Traverse City, Mich.

Continuing with reference to FIG. 6A, the servomotor assembly 300 may further comprise a number of bearings 328 positioned to facilitate rotational motion of the internal hardware components. In another embodiment, an internal mechanical static hardstop 327 and a rotational range of motion (ROM) hardstop 329 are included, such as by constructing each into a housing of the servomotor assembly 300, to prevent the patient/user from exceeding a safe range of motion during testing, exercise, or rehabilitation. A motor temperature sensor is also integrated into the servomotor assembly 300 for safe operation. An embedded firmware system includes additional safety monitoring to disable motor power in the event of limit exceedance.

With reference now to FIG. 6B, the servomotor assembly 300 further comprises a sensor assembly 330 having two sensor sub-assemblies. One sensor sub-assembly is a motor position sensor sub-assembly 331 used for measuring rotational position of the rotor shaft 326 (see FIG. 6A) to determine positional values and thereby enable computation of rotational velocity of rotor shaft 326 by embedded control system 400. The other sensor sub-assembly is a torque sensor sub-assembly 332 used for measuring torque imparted via the distal limb lever assembly 350 by a patient/user. In one embodiment, the components of the position sensor assembly 331 comprise an optical encoder disk 333 and an optical encoder read head 335 positioned as shown in FIGS. 6A and 6B. In another embodiment, the components of the torque sensor sub-assembly 332 comprise one or more strain gauges 334 mounted to rigid torque sensor shaft 336 as shown in FIG. 6B.

FIG. 6C is another perspective view of the servomotor assembly 300 showing additional exterior structural components. In one embodiment, servomotor assembly 300 further comprises the handle 302, a structural bone 304, the knob/bone mounting assembly 306 (not shown in FIG. 6C but visible in FIG. 1), the rotatable output yoke 308, and a conduit 307. As described previously, the knob/bone mounting assembly 306 enables the structural bone 304 to mount securely to base 200 once placed in the servomotor receptacle 204a/204b. The structural bone 304 also provides a housing of electrical parts and wiring for communication of electronic data measured by sensor assembly 330 for collection by embedded control system 400 via conduit 307.

Portable System Control

Any reference to the term "user-specified" in the text appearing below indicates an operative mode in which a system operator has selected an input or value via an application running on a computer that is operatively connected and thereby interfaced with an embedded control system, such as a connection via a Universal Serial Bus (USB) interface port or other comparable interface port. In one embodiment, a method of performing the human-machine interface is via a graphical user interface or GUI. In the description provided below, such GUI is called "kdgui."

Multi-Loop Cascaded Control

The control architecture of system 100 leverages a multi-loop cascaded control approach. As can be seen in the mode-specific feedback control diagrams of FIGS. 7-9, more than one control loop are cascaded down to ultimately determine what real-time motor voltage command should be sent to the motor. For most exercise modes, the order of the cascaded controller, from highest to lowest, is Torque—Velocity—Current Motor voltage command. This architecture offers the easy capability to install control limits at each loop, whether they are for performance behavior or safety or other. For example, in the passive mode diagram of FIG. 7, the output of the Torque Loop is an unlimited velocity command. However, if the user has chosen a passive velocity of 120 deg/s, for example, this "limit" is then used to limit the unlimited velocity command, prior to the Velocity Loop executing. Torques, Velocities, Currents, Positions, and Voltages can all easily be limited to user-specified or hard-coded values in this manner.

Passive Mode

In "passive mode", the system 100 moves at the user-specified velocity and stops when the user resists motion with a torque magnitude at least as high as the user-specified torque threshold. Upon reaching the system flexion (or extension) angle related to the user range-of-motion limits previously captured, apparatus motion will pause for a user-specified number of seconds. After the pause, the system 100 will move in the opposite direction at the user-specified velocity. This back-and-forth motion will repeat until user action is taken to halt it.

The operator/user specifies two parameters: 1) rotational velocity setpoint; and 2) torque threshold value.

Commanded velocity magnitude is limited between zero and the user-specified velocity, in the direction of movement.

Torque command is set to the user-specified torque threshold. If the torque threshold is not met (user is not resisting system motion with sufficient torque), the system continues to move at the user-specified velocity. When the torque threshold is met by the user, the system stops moving (since the velocity command is limited to zero in that direction). When the measured torque subsequently drops below the torque threshold, the system will continue its motion.

Figure 7:
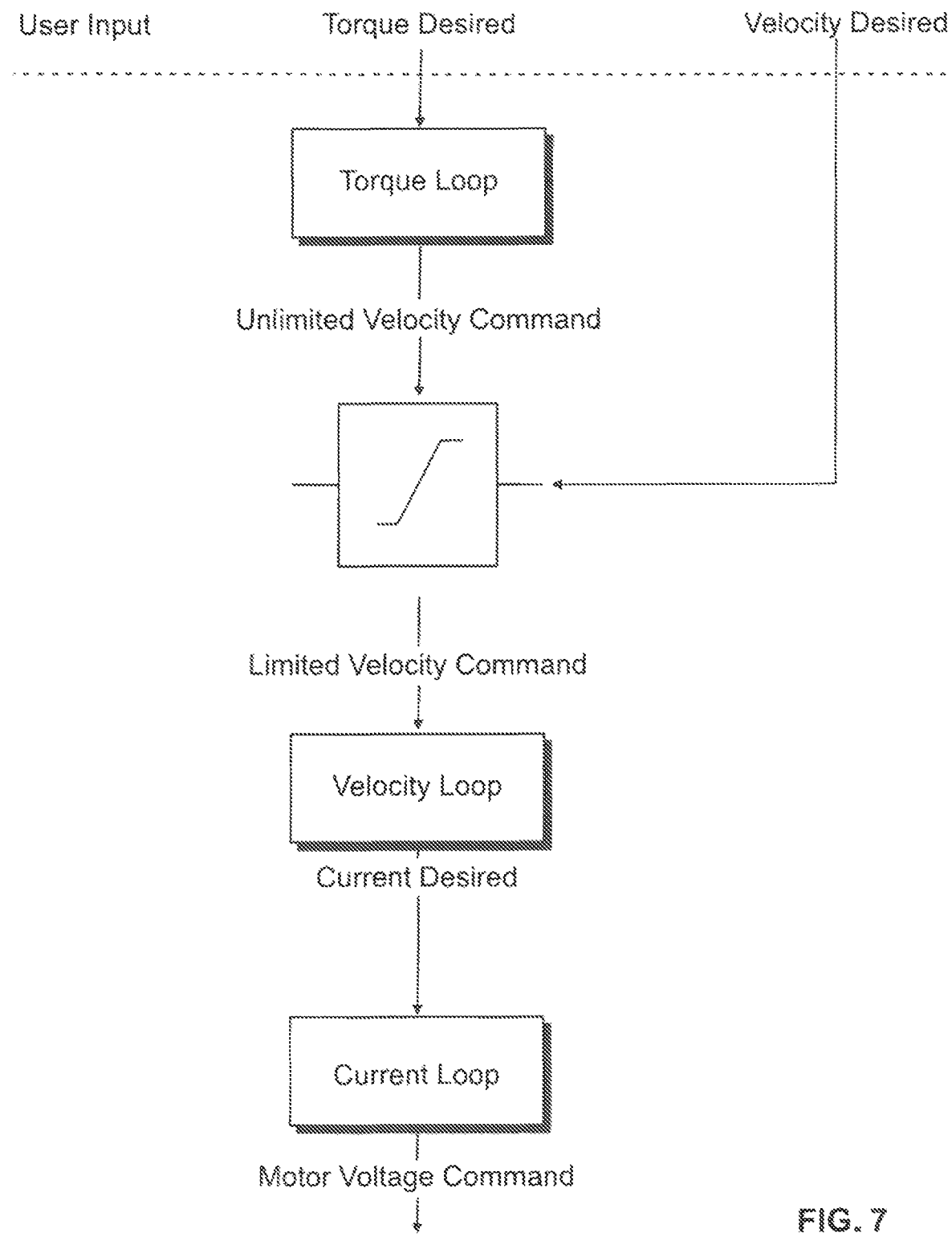
FIG. 7 is a graphical representation of a cascaded closed-loop feedback control for a "passive mode" operation of an embedded control system in accordance with embodiments described herein.

A graphical depiction of the method for Passive Mode closed-loop control is shown generally in FIG. 7.

Isokinetic Mode

In "isokinetic mode", the system 100 follows the user's motion, but it prevents the user from moving faster than a specified velocity.

The user specifies two parameters: 1) velocity limit in the extension direction and 2) velocity limit in the flexion direction.

A torque command of zero is the input to the controller's torque loop. The controller will closely maintain a measured torque of zero, assuming the user-driven velocity magnitude remains below the user-specified velocity for the given direction. In the case where the user moves the system with enough velocity to match the user-specified velocity for the given direction, the controller will limit the velocity to the user-specified velocity. The user may continue to attempt to push the system at a faster velocity, but the system will closely maintain its user-specified velocity, in which case the measured torque will increase. The torque loop's function of maintaining zero torque is hereby limited by this velocity limit.

In isokinetic mode, all motion is user-driven. If the user applies no motion to the system, the system will seek its zero torque state, which is hanging straight down.

Figure 8:
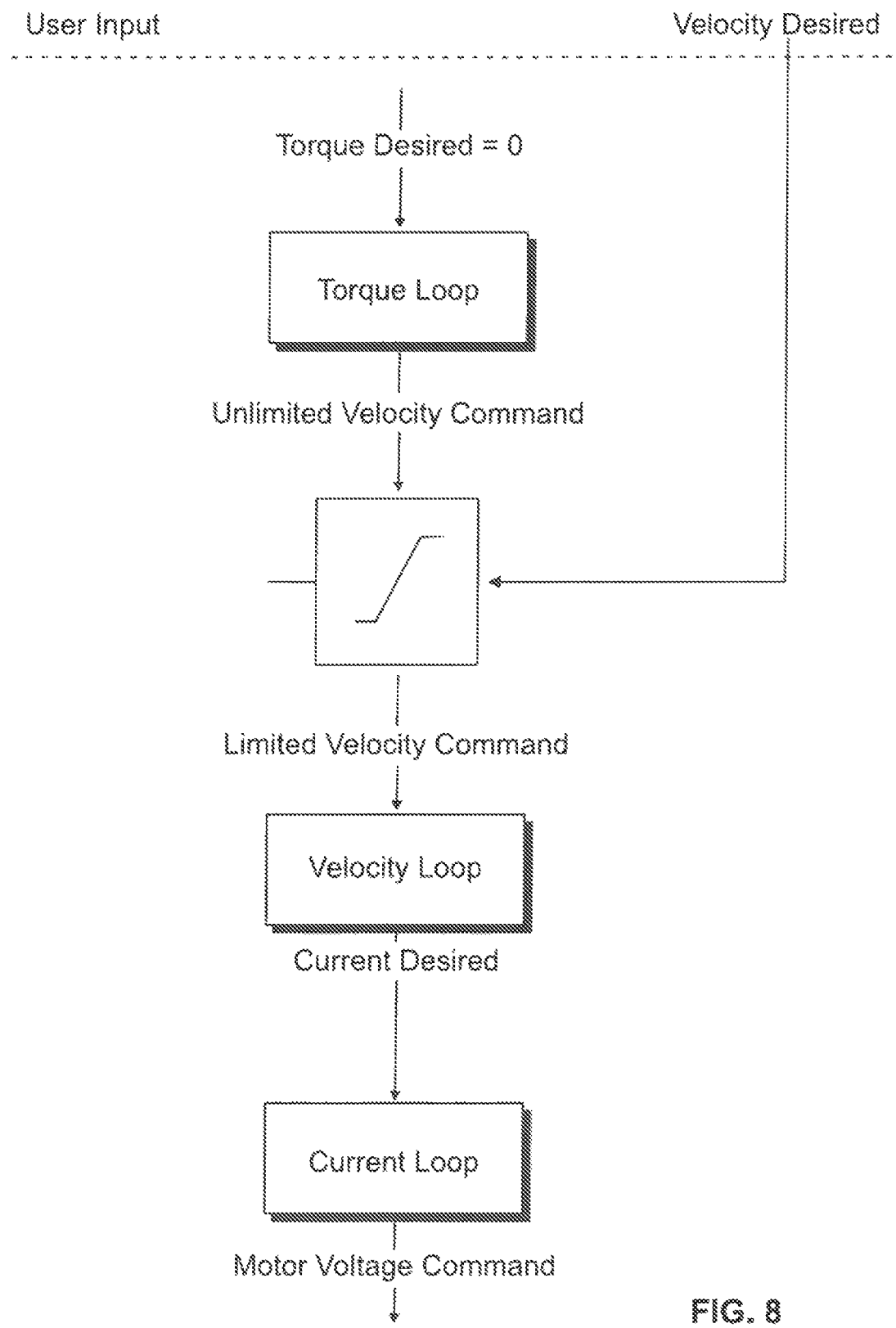
FIG. 8 is a graphical representation of a cascaded closed-loop feedback control for an "isokinetic mode" of operation for an embedded control system in accordance with embodiments described herein.

A graphical depiction of the method for Isokinetic Mode closed-loop control is shown generally in FIG. 8.

Isometric Mode

In an "isometric mode" of operation, the portable system remains in its current position and prevents motion or rotation of the servomotor assembly in either direction.

The only parameter specified by the user is the position target for the system to hold. This target is captured by latching the current position upon user entry into an "Isometric Mode." The system will continue to hold its position until the "Isometric Mode" is exited via user input.

Figure 9:
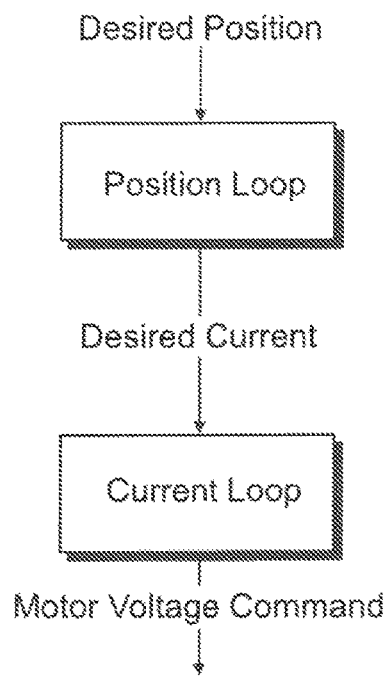
FIG. 9 is a graphical representation of an "isometric mode" of operation for an embedded control system in accordance with embodiments described herein.

A graphical depiction of the method for closed-loop control of the system 100 in an isometric mode controller is shown generally in FIG. 9.

Software Cushions

Figure 10:
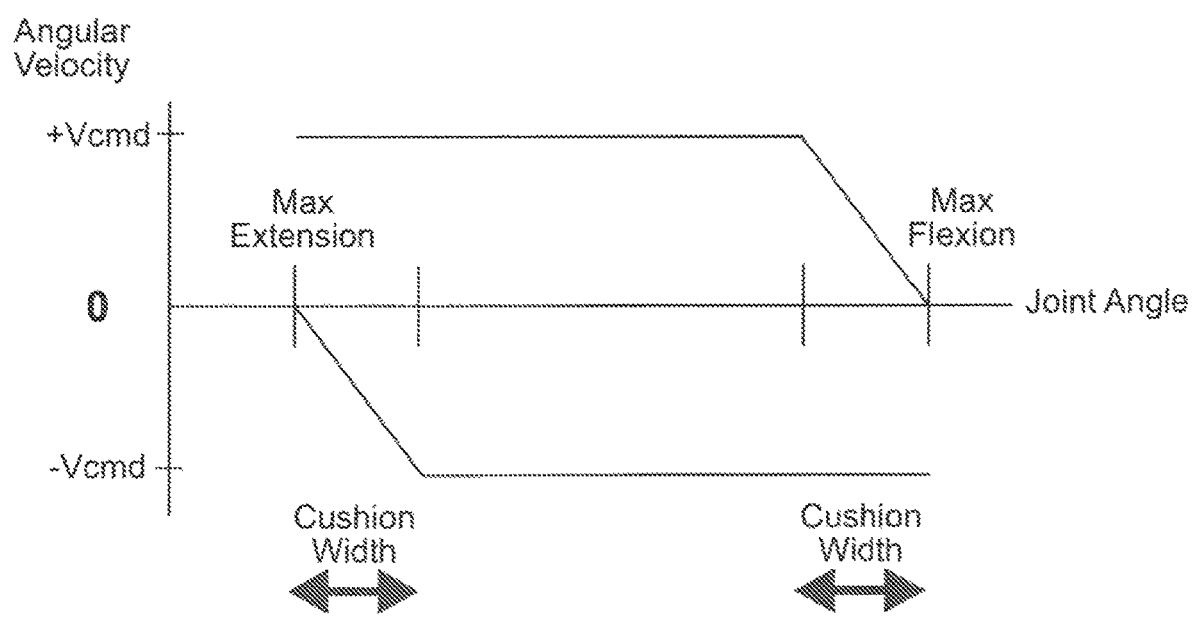
FIG. 10 is a graphical representation of software cushions implemented as part of the embedded control system for embodiments described herein.

Referring now to FIG. 10, software cushions have been implemented to allow for a smooth transition to a stop during motion near the end of safe travel. The software cushion effectively decreases the maximum allowable velocity command toward the user's range of motion (ROM) to zero, such that the controller will increasingly resist motion toward the user ROM as the joint angle approaches the user ROM.

The joint angle range where the cushions are active are within the "cushion width" from the user end of ROM. Cushion widths are defined as a function of a) target velocity in the given mode and b) selection of hard or soft cushion at the application level. In one embodiment, the hard cushion width is defined as 20 deg per 240 deg/s of target velocity, and the soft cushion width is defined as 40 deg per 240 deg/s of target velocity. For example, if the target velocity is a 120 deg/s isokinetic, a hard cushion width would be 10 deg, and the soft cushion width would be 20 deg. The cushion functionality only operates when the magnitude of the difference between current joint angle and user ROM limit is less than the defined cushion width. Outside of this range, the cushion is inactive and no cushion-related velocity command limiting is performed. Within the software cushion, the functionality is simple, once having the benefit of this disclosure.

To illustrate, consider another embodiment where the cushion width is 10 deg, the target velocity is 120 deg/s isokinetic, and the extension end of the user range of motion (ROM) is 0 deg. In this scenario, the cushion would be active between 0 deg and +10 deg. At an angle of +10 deg, the cushion starts to be active. At an angle of 4-5 deg, the maximum allowable velocity command toward the end of user ROM would be 60 deg/s. At an angle of +2.5 deg, the maximum allowable velocity command toward the end of user ROM would be 30 deg/s. In this scenario, the maximum allowable velocity command away from the end of the user ROM is unchanged, and remains at 120 deg/s. Cushion widths are automatically recalculated whenever the system mode or the target velocity is changed by the user.

Although only a few exemplary embodiments have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, while a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A portable dynamometer for a human joint, comprising:
    a base to be positioned and secured upon a surface;
    a servomotor assembly, operatively connected to the base and readily detachable therefrom, for measuring positional values and torque values associated with motion of the human joint;
    an embedded control system, operatively connected to the servomotor assembly, for controlling rotational velocity of a rotor located in the servomotor assembly and for collecting positional values and torque values measured by the servomotor assembly;
    a physical human-machine interface for securing the human joint into a stable position for use of the portable dynamometer in an ambidextrous and readily repeatable manner;
    a user interface sub-system for selecting operative modes and input parameters of the portable dynamometer and for real-time processing and display of collected values and storing of such collected values as electronic data; and,
    an electric power source.

2. The portable dynamometer of claim 1, wherein the operative modes of the portable dynamometer comprise passive mode, isokinetic mode, and isometric mode.

3. The portable dynamometer of claim 1, wherein the base is configured to enable mounting and detachment of the servomotor assembly on both the right side and the left side of a human test subject and to enable operational mounting of the embedded control system.

4. The portable dynamometer of claim 1, wherein the base is configured to enable operational mounting of the embedded control system.

5. The portable dynamometer of claim 1, wherein the physical human-machine interface is capable of readily making repeatable sizing adjustments to fit human test subjects within a large anthropometric range, the physical human-machine interface further comprising:
    an adjustable set of straps, operatively connected to the base, one set of straps for stabilizing the human test subject at the thigh, the other set of straps stabilizing the human test subject at the waist; and,
    an adjustable ambidextrous distal limb attachment assembly, operatively connected to the servomotor assembly, the limb attachment assembly enabling multiple degrees of freedom for positioning and securing to a limb of a human test subject sized within the large anthropometric range.

6. The portable dynamometer of claim 5, wherein the physical human-machine interface further comprises an adjustable seat backrest, operatively connected to the base, for positioning a rotation of axis of the human joint in a position substantially collinear with a rotational axis of the servomotor assembly.

7. The portable dynamometer of claim 5, wherein the large anthropometric range of human test subject includes the smaller 5th percentile to the larger 95th percentile of adult humans of both sexes.

8. The portable dynamometer of claim 7, wherein the human joint is a knee.

9. The portable dynamometer of claim 1, wherein the embedded control system is configured for real-time communication of collected positional values and torque values and of computed rotational velocity values as electronic data to the user interface sub-system and wherein the user interface sub-system comprises one of a personal computer, a tablet, a smart phone, a smart watch and other computing device having an electronic display.

10. An exercise and rehabilitation apparatus, comprising:
    a base to be positioned and secured upon a surface;
    a servomotor assembly, operatively connected to the base and readily detachable therefrom, for measuring positional values and torque values associated with motion of a human joint;
    an embedded control system, operatively connected to the servomotor assembly, for controlling rotational motion of a rotor located in the servomotor assembly and collecting positional values and torque values measured by the servomotor assembly;
    a physical human-machine interface for securing the human joint into a stable position for use of the apparatus in an ambidextrous and readily repeatable manner;
    a user interface sub-system for selecting operative modes and input parameters of the apparatus and for real-time processing and display of the collected values and storing of the collected values as electronic data; and, an electric power source.

11. The apparatus of claim 10, wherein the base is configured to enable mounting and detachment of the servomotor assembly on both the right side and the left side of a user and to enable operational mounting of the embedded control system.

12. The apparatus of claim 10, wherein the base is configured to enable operational mounting of the embedded control system.

13. The apparatus of claim 12, wherein the large anthropometric range of user includes the smaller 5th percentile to the larger 95th percentile of adult humans of both sexes.

14. The apparatus of claim 13, wherein the human joint is a knee.

15. The apparatus of claim 10, wherein the physical human-machine interface is capable of readily making repeatable sizing adjustments to fit users within a large anthropometric range, the physical human-machine interface further comprising:
    an adjustable set of straps, operatively connected to the base, one set of straps for stabilizing the user at the thigh, the other set of straps stabilizing the user at the waist; and,
    an adjustable ambidextrous distal limb attachment assembly, operatively connected to the servomotor assembly, the limb attachment assembly enabling multiple degrees of freedom for positioning and securing to a limb of users sized within the large anthropometric range.

16. The apparatus of claim 15, wherein the physical human-machine interface further comprises an adjustable seat backrest, operatively connected to the base, for positioning a rotation of axis of the human joint in a position substantially collinear with a rotational axis of the servomotor assembly.

17. The apparatus of claim 10, wherein the embedded control system is configured for real-time communication of collected positional values and torque values and of computed rotational velocity values as electronic data to the user interface sub-system and wherein the user interface sub-system comprises one of a personal computer, a tablet, a smart phone, a smart watch and other computing device having an electronic display.

18. A method for determining strength of an isolated muscle group of a human joint, comprising the steps of:
    mounting and securing a detachable servomotor assembly of a portable dynamometer upon a surface;
    securing the human joint to be tested into a stable position with an adjustable, ambidextrous distal limb attachment assembly for use of the portable dynamometer in a readily repeatable manner;
    selecting an operative mode of the portable dynamometer;
    powering rotational motion of the detachable servomotor assembly when required for the selected operative mode;
    controlling rotational velocity of the detachable servomotor assembly;
    measuring positional values and torque values associated with motion of the stabilized human joint; and
    collecting the positional values and the torque values that are measured by the detachable servomotor assembly.

19. The method of claim 18, further comprising the steps of:
    detaching the servomotor assembly after performing the steps of measuring values and collecting values for the first stabilized human joint;
    mounting and securing the detachable servomotor assembly on a contralateral side of a human test subject to determine muscle strength of a second human joint, the second human joint being a similar type of joint as the first stabilized human joint of the human test subject;
    securing the second human joint into a stable position for use of the portable dynamometer in an ambidextrous and readily repeatable manner;
    selecting an operative mode of the portable dynamometer;
    powering rotational motion of the detachable servomotor assembly when required for the selected operative mode;
    controlling rotational velocity of the detachable servomotor assembly;
    measuring positional values and torque values associated with motion of the second stabilized human joint; and
    collecting the positional values and the torque values that are measured by the detachable servomotor assembly for the second stabilized human joint.

* * * * *